United States Patent [19]

Kleinlogel et al.

[11] 4,380,550
[45] Apr. 19, 1983

[54] GUANFACINE IN TREATING OPIATE ADDICTION

[75] Inventors: Horst Kleinlogel, Hinterkappelen; Carl Theohar, Basel, both of Switzerland

[73] Assignee: Sandoz Ltd., Basel, Switzerland

[21] Appl. No.: 383,080

[22] Filed: May 28, 1982

[30] Foreign Application Priority Data

Jun. 1, 1981 [GB] United Kingdom ................ 8116751

[51] Int. Cl.$^3$ ............................................ A61K 31/165
[52] U.S. Cl. ..................................................... 424/324
[58] Field of Search ......................................... 424/324

[56] References Cited

U.S. PATENT DOCUMENTS 3,632,645  1/1972  Bream ................................ 260/588

OTHER PUBLICATIONS

Gold, M. S., et al., JAMA 243, pp. 343–346 (1980).
Chem. Abst., vol. 93, 125576u (1980).
Chem. Abst., vol. 90, 115374a, 1979.
Washton, A. M. et al., The Lancet, pp. 991 & 992, (5-2-81).
Gold, M. S. et al., The Lancet, pp. 992 & 993, (5-2-81).

*Primary Examiner*—Stanley J. Friedman
*Attorney, Agent, or Firm*—Gerald D. Sharkin; Robert S. Honor; Joseph J. Borovian

[57] ABSTRACT

This invention provides a new opiate withdrawal use of an guanidine derivative and novel pharmaceutical compositions for such use.

5 Claims, No Drawings

GUANFACINE IN TREATING OPIATE ADDICTION

The present invention relates to a new use for the compound of formula I,

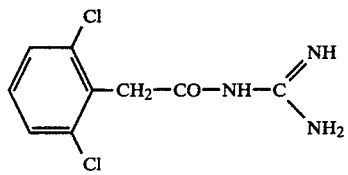

which is the compound N-amidino-2-[2,6-dichlorophenyl]acetamide, also known and referred to throughout the present specification and claims as Guanfacine.

Guanfacine as well as processes for its production are known e.g. from U.S. Pat. No. 3,632,645. The compound is an antihypertensive, commercially available under the name Estulic.

In accordance with the present invention it has now been found that Guanfacine is indicated for use as a non-abusable (i.e. non-addictive), opiate substitute in the treatment of opiate addiction, e.g. addiction to morphine, methadone, heroin or heroin administered in conjunction with other opium derivatives, barbiturates, amphetamines or tranquillizers. In particular, it has been found that on administration to opiate addicts Guanfacine satisfies or compensates for the physical requirements of addiction and minimizes or even prevents the occurrence of withdrawal symptoms. At the same time it has been found that Guanfacine does not itself induce physical dependency. Accordingly Guanfacine may be used as an acceptable alternative for the treatment of opiate addiction by substitution therapy. Moreover, after a suitable interval, substitution therapy using Guanfacine may be discontinued, after a drug reduction phase during which the daily dosage of the compound administered may be successively decreased with minimal occurrence of withdrawal symptoms or other negative side effects, so as to wean the opiate addict from opiate dependency.

Guanfacine is well tolerated during the substitution therapy but may induce minimal signs of sedation, depression and insignificant or acceptable levels of hypotension.

The present invention accordingly provides a method of treating symptoms arising on withdrawal of opiate administration from an opiate addict which method comprises administering to said subject an effective amount of Guanfacine in free base form or in pharmaceutically acceptable acid addition salt form.

The efficacy of Guanfacine in the treatment of opiate addiction may be demonstrated in clinical trials, effected for example in accordance with the following general methods:

In one series of trials groups of about 10 test-subjects are selected from hospitalised patients of known case-history including long-term heroin addiction. The subjects are kept under strict observation throughout and subsequent to the trial period. They are allowed no access to heroin and their physical and psychological condition is monitored regularly.

Guanfacine is administered from day one of the trial onwards to each test-subject individually at the onset of withdrawal symptoms. The initial dosage and frequency of administration is gauged on the basis of the known severity of addiction, administration being repeated each time withdrawal symptoms occur. The dose used is generally not so high that an unacceptable level of hypotension occurs. Generally the initial dosage is selected and then standardised for each subject to provide a daily dosage of from 0.01 to 0.25 mg/day or, in the case of subjects exhibiting greater drug resistance, up to 0.5 or 1 mg or even up to 4 mg/day. Administration may be effected orally or intravenously in unit dosage form from 1 to 5 times daily depending on the frequency with which withdrawal symptoms occur. Such symptoms are well known and include pronounced intensity of (i) psychic feelings such as anxiety or fear, and cravings for opiate, (ii) general autonomic signs such as yawning, perspiration, lacrimation, rhinorrhea, mydriasis, palpitation, hot and cold "flashes", gooseflesh, and spontaneous orgasm or ejaculation, (iii) neuromuscular signs such as restlessness, aching bones and muscles, tremors and weakness, (iv) gastrointestinal signs such as abdominal cramps, diarrhea, nausea and loss of appetite and (v) sleep disturbances such as difficulty in falling asleep and interrupted sleep. The responsiveness of the subject to Guanfacine therapy, e.g. the degree to which the occurrence of withdrawal symptoms is excluded, is determined and monitored using standard Check Lists. For example, the Opiate Withdrawal Check List has been developed by Sandoz to specifically monitor the presence and intensity of the significant signs and symptoms of opiate withdrawal. It records known 21 indications and symptoms of opiate withdrawal, and 4 major physiological parameters [blood pressure, pulse rate, temperature and respiratory rate]. The frequency of application of the Check List may be from 1 to 7 times daily depending on the day of withdrawal being assessed. While it can be used alone, its use may be combined with other symptoms from other known Check Lists, such as for example the Global Impression scale and/or the Fischer Symptom Check List, to control for symptoms not related to opiate withdrawal.

Therapy is continued over a period of from about 5 days to 2 weeks. During this period the initially administered dosage is successively reduced, the rate of reduction being determined for each subject on the basis of the observed efficacy of therapy at each phase of the trial. Therapy is eventually discontinued altogether. Monitoring of the subject's condition, in particular to detect the occurence of withdrawal symptoms attributable either to withdrawal from opiates or from the substitute Guanfacine used in the therapy, continued throughout the trial for a period of from about 5 days to about 2-3 weeks. If desired, Guanfacine may be co-administered with other drugs, e.g. hypnotics, if certain withdrawal symptoms such as sleep disturbances do not diminish.

One trial was effected on 9 hospitalized heroin addicts. 5 males and 4 females, average aged 26 years, had injected heroin for more than one year in doses of 500 mg to 4 g daily. The maximum doses reported during the last weeks prior to treatment were 3–4 g. They had been addicted to heroin for 1–10 years. Guanfacine was administered at morning and at evening. The 1st day patients received an average dosage of 0.55 mg, the 2nd day 0.85 mg, the 3rd day 0.95 mg, the 4th day 0.7 mg, the 5th day 0.9 mg, the 6th day 0.1 and the 7th day 0.05 mg. The average treatment duration was 4.4 days. The average duration of stay in the hospital was 8.1 days.

Sleep disturbances were treated with 100 mg doxepine and additionally for the first 3 days with 100 mg oxazepam. During the trial the patients completed a 48 symptom check-list. The symptoms were headache, tiredness, disturbances of equilibrium, difficulty in breathing, feeling of asphyxia, tendency to cry, lack of appetite, hiccups, heart palpitations, easy exhaustion, fear, abdominal pains, constipation, lack of energy, bone and muscle pains, impairment of concentration, cold feet, lack of sexual excitement, quick to blush, shivering, heat waves, sad thoughts, inner tension, numbness, chocking in the throat, short windedness, weakness, swallowing difficulties, pains in the breast, feelings of pressure and fullness in abdomen, faintness, nausea, heartburn, irritability, brooding, heavy sweating, back pains, inner unrest, tiredness in legs, restlessness in legs, sensitivity to heat, sensitivity to cold, excessive need of sleep, insomnia, vertigo, trembling, neck and shoulder pains and loss of weight. In addition all patients completed a self-rating scale of general well-being and an affectivity profile. Blood pressure has been measured 3 times a day. Laboratory tests have been performed before and at the end of the trial. Muscoskeletal pains which increased on day 2-4 were markedly reduced in intensity at the end of the trial. On the 2nd, 3rd and 4th day of withdrawal, gastrointestinal disturbances (pains, nausea) were present, but these almost disappeared at the end of the trial. There were no changes in the blood pressure readings during administration of the drug. Laboratory tests were within the normal range. There were significant decreases in inter alia inner unrest, inner tension, lack of energy, tiredness, vertigo and sadness.

In a second trial effected in analogous manner, satisfactory results were obtained using capsules of Guanfacine at a dose of 8 capsules of 0.01 mg every 2 hours or 0.1 mg 3 times a day.

In a third trial out of 30 hospitalized patients 11 were addicted to heroin, 6 to heroin and opium derivatives, 10 to heroin and barbiturates, amphetamines or tranquillizers and 3 to methadone. They had been addicted for 3-5 years. 12 of them were women. The average age was 25 years. 24 of them expressed voluntarily interest in discontinuing use of opiate, 2 of them had a medical illness and 4 of them discontinued for juridical and family reasons. The duration of the trial was in average 7 days.

11 patients interrupted the trial for various reasons. 19 patients completed the withdrawal trial.

For the first 3 days to one group of patients Guanfacine was administered at a dosage of 0.5 mg every 4 hours. This dosage was progressively decreased. The other group of patients received 0.5 mg Guanfacine every 6 hours for 5 days and decreased dosages for 3 days. On the 2nd or 3rd day 17 patients received analgesics on their request. All patients received tranquillizers and hypnotics. Untoward side effects never caused interruption of Guanfacine administration. In 21 patients the blood pressure was moderately decreased (1 to 2 points). This decrease was observed in 17 patients from the 1st day on, but a normalisation occurred on the 2nd day. For 4 patients the normalisation took longer, e.g. until the end of the trial, on the 7th or 8th day. 8 patients did not show any somnolence. For the remaining 22 patients their somnolence was moderate. All patients had sleep difficulties which were relieved by the administration of a hypnotic.

Successful withdrawal was accomplished with 19 of the 30 subjects.

The results indicate that Guanfacine is useful as an effective non-addictive opiate substitute. At appropriate dosages the severity of withdrawal symptoms may be brought within tolerable limits or their occurrence prevented. Guanfacine is well tolerated by all subjects undergoing therapy and no significant detrimental side-effects may be observed, e.g. sedation, depression or unacceptable hypotension. Especially noteworthy in the latter connection is the absence of withdrawal symptoms directly caused by reduction of discontinuation of the administration of Guanfacine.

The dosage employed in accordance with the method of the invention will of course vary according to, inter alia, the mode of administration, the condition of the subject to be treated, in particular the severity of addiction and previous case-history (where known), and on the phase of therapy reached. In particular the choice of a suitable course for substitution therapy leading to ultimate withdrawal from drug dependency, e.g. the rate at which the daily dosage is reduced and the timing of termination of therapy, will vary having regard to the subject's general e.g. physical and psychological responsiveness.

In general, however, Guanfacine will be administered at a daily dosage below that required to lead to unacceptable hypotension (e.g. 10 to 20 mmHg below normal). Suitable daily dosages are in general in the range of about 0.01 mg to about 4 mg, for example about 0.01 mg to about 2 mg, more usually about 0.03 mg to about 1.0 mg, or for example from about 0.08 mg to about 4.0 mg, the higher dosages being used at the onset of treatment. The compound may be administered p.o. or i.v. in unit dosage form, 1 to 5 times per day and suitable unit dosage forms containing from about 0.002 to about 4 mg, usually from about 0.002 to about 1 mg Guanfacine per unit dosage. Conveniently Guanfacine is administered in unit dosage form containing about 0.01 mg to about 0.25 mg, particularly orally.

In accordance with the invention Guanfacine may be administered in free base form or in pharmaceutically acceptable acid addition salt form. Such acid addition salt forms are also known and include the hydrochloride and oxalate. Preferably the hydrochloride is used.

The activity of such pharmaceutically acceptable salt forms will generally be of the same order as that of the respective free base form. As used herein all amounts of such compounds recited refer to the amount of the free base form unless otherwise indicated.

Pharmaceutical compositions for use in the method of the invention may be prepared in accordance with standard techniques for example by admixture of the active ingredient with conventional compatible pharmaceutically acceptable diluents or carriers, e.g. to prepare solid preparations such as capsules or injectable solutions or suspensions suitable for i.v. administration. Capsule formulations may contain Guanfacine on its own or together with an inert solid diluent, for example, lactose, starch, colloidal silicon dioxide and microcristalline cellulose. Solutions or suspensions may include e.g. suspending agents such as methylcellulose, tragacanth and sodium alginate, wetting agents such as lecithin, polyoxyethylene stearate and polyoxyethylene sorbitan monooleate and preservatives such as ethyl-p-hydroxy-benzoate. They will generally be presented in sterile ampoule forms suitable for injection. Such forms also include, e.g. known disposable syringe forms. The following examples illustrate compositions suitable for use in the method of the invention: Avicel as used hereinafter is a form of microcrystalline cellulose. Aerosil as used hereinafter is a form of colloidal silica. Suppliers of these forms and their properties may be found in H. P. Fiedler, Lexikon der Hilfsstoffe für Pharmazie, Kosmetik, und angrenzende Gebiete, 2nd Edition Editio Cantor, Aulendorf, W. Germany.

EXAMPLE 1

Capsule suitable for oral administration

Capsules containing the ingredients indicated below may be prepared by conventional techniques.

| Ingredient | Weight (mg) | |
|---|---|---|
| Guanfacine hydrochloride | 0.0115 | (~0.01 mg base) |
| Lactose | 144.5385 | |
| Avicel$^R$ PH 101 | 19.6 | |
| Aerosil$^R$ 200 | 0.85 | |
| Stearic acid | 5.0 | |
| | 170.00 | |

Other capsule formulations are as follows:

| | Capsule | |
|---|---|---|
| Ingredient | Weight (mg) | |
| Guanfacine hydrochloride | 0.288 | 1.15 |
| | (~0.25 mg base) | (~1 mg base) |
| Lactose | 144.262 | 143.4 |
| Avicel$^R$ PH 101 | 19.6 | 19.6 |
| Aerosil$^R$ 200 | 0.85 | 0.85 |
| Stearic acid | 5.0 | 5.0 |
| | 170.00 | 170.00 |

EXAMPLE 2

Sterile solution for injection

A solution for injection containing the ingredients indicated below may be prepared by conventional techniques, sterilised and filled into pre-sterilised ampoules of 2 ml capacity suitable for injection.

| Ingredient | Weight/Volume |
|---|---|
| Guanfacine hydrochloride | 0.6028 mg/ml |
| | (~0.5 mg base) |
| Sodium chloride | 9.000 mg/ml |
| 0.1 N Hydrochloride acid at pH 3.7 | q.s. |
| Distilled water | to 1 ml |

We claim:

1. A method of treating symptoms arising on withdrawal of opiate administration from an opiate addict which method comprises administering to said subject an effective amount of Guanfacine of the formula I:

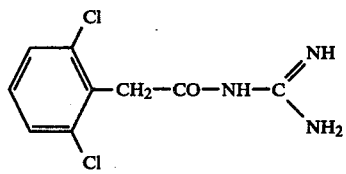

in free base form or in pharmaceutically acceptable acid addition salt form.

2. A method according to claim 1 wherein the Guanfacine is administered at a daily dosage of from about 0.01 to about 2 mg.

3. A method according to claim 1 wherein the Guanfacine is administered at a daily dosage of from about 0.03 to about 1 mg.

4. A method according to claim 1 wherein the Guanfacine is administered in unit dosage form containing from 0.01 to 0.25 mg of Guanfacine.

5. A method according to claim 1 wherein the Guanfacine is administered in unit dosage form containing from 0.002 to 1 mg of Guanfacine.

* * * * *